(12) United States Patent
Kuo et al.

(10) Patent No.: US 11,270,033 B2
(45) Date of Patent: Mar. 8, 2022

(54) PROSTHODONTIC AND ORTHODONTIC APPARATUS AND METHODS

(71) Applicant: ALIGN TECHNOLOGY, INC., San Jose, CA (US)

(72) Inventors: Eric Kuo, San Jose, CA (US); Jihua Cheng, Cupertino, CA (US); Vadim Matov, San Jose, CA (US); Juan Carlos Alvarez, Gilroy, CA (US); Ali Kakavand, San Carlos, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 460 days.

(21) Appl. No.: 16/189,826

(22) Filed: Nov. 13, 2018

(65) Prior Publication Data

US 2019/0080029 A1 Mar. 14, 2019

Related U.S. Application Data

(60) Continuation of application No. 15/700,011, filed on Sep. 8, 2017, which is a division of application No.
(Continued)

(51) Int. Cl.
*G06F 30/00* (2020.01)
*A61C 7/00* (2006.01)
(Continued)

(52) U.S. Cl.
CPC .............. *G06F 30/00* (2020.01); *A61C 7/002* (2013.01); *A61C 7/08* (2013.01); *A61C 9/004* (2013.01);
(Continued)

(58) Field of Classification Search
CPC .......... G06F 30/00; G06F 30/10; G06F 30/12; G06F 2111/00; G06F 2111/10;
(Continued)

(56) References Cited

U.S. PATENT DOCUMENTS 6,587,828 B1 7/2003 Sachdeva
6,632,089 B2 10/2003 Rubbert et al.
(Continued)

FOREIGN PATENT DOCUMENTS

JP 09-253103 9/1997
JP 2005-503235 2/2005
(Continued)

OTHER PUBLICATIONS

Non-Final Office Action on co-pending (U.S. Appl. No. 15/700,011) dated Apr. 3, 2020.
(Continued)

*Primary Examiner* — Nicholas D Lucchesi
*Assistant Examiner* — Mirayda A Aponte
(74) *Attorney, Agent, or Firm* — FisherBroyles, LLP

(57) ABSTRACT

System and method for developing a treatment plan for achieving a treatment goal including creating a virtual model of a dental patient's dentition; transforming the virtual model of the dentition using virtual prosthodontics to facilitate achievement of the treatment goal; transforming the virtual model of the dentition using virtual orthodontics to facilitate achievement of the treatment goal; iterating on the transforming steps until substantially achieving the treatment goal; and generating an orthodontic treatment plan and a prosthodontic treatment plan based upon the substantially achieved treatment goal.

20 Claims, 14 Drawing Sheets

Related U.S. Application Data

14/461,281, filed on Aug. 15, 2014, now abandoned, which is a continuation of application No. 12/682,225, filed as application No. PCT/US2007/081262 on Oct. 12, 2007, now Pat. No. 8,807,999.

(51) Int. Cl.
*A61C 7/08* (2006.01)
*G16H 50/50* (2018.01)
*A61C 13/00* (2006.01)
*A61C 9/00* (2006.01)

(52) U.S. Cl.
CPC ......... *A61C 13/0004* (2013.01); *G16H 50/50* (2018.01)

(58) Field of Classification Search
CPC . G06F 2111/16; G06F 2111/18; G16H 50/50; A61C 7/002; A61C 7/08; A61C 9/004; A61C 13/0004
USPC .......................................................... 433/24
See application file for complete search history.

(56) References Cited

U.S. PATENT DOCUMENTS

| | | | |
|---|---|---|---|
| 6,648,640 | B2 | 11/2003 | Rubbert et al. |
| 7,029,275 | B2 | 4/2006 | Rubbert et al. |
| 7,080,979 | B2 | 7/2006 | Rubbert et al. |
| 7,134,874 | B2 | 11/2006 | Chishti et al. |
| 7,156,655 | B2 | 1/2007 | Sachdeva et al. |
| 7,361,018 | B2 | 4/2008 | Imgrund et al. |
| 7,658,610 | B2 | 2/2010 | Knopp |
| 8,105,080 | B2 | 1/2012 | Chishti et al. |
| 2001/0002310 | A1 | 5/2001 | Chishti et al. |
| 2003/0203334 | A1 | 10/2003 | Hedge et al. |
| 2004/0110110 | A1 | 6/2004 | Chishti et al. |
| 2005/0010450 | A1 | 1/2005 | Hultgren et al. |
| 2005/0208449 | A1 | 9/2005 | Abolfathi et al. |
| 2005/0214710 | A1 | 9/2005 | Erskine-Smith |
| 2005/0271996 | A1 | 12/2005 | Sporbert et al. |
| 2006/0121408 | A1 | 6/2006 | Hedge et al. |
| 2006/0190301 | A1 | 8/2006 | Sachdeva |
| 2006/0275731 | A1 | 12/2006 | Wen et al. |
| 2006/0275736 | A1 | 12/2006 | Wen et al. |
| 2007/0128574 | A1 | 6/2007 | Kuo et al. |
| 2007/0231765 | A1 | 10/2007 | Phan et al. |
| 2008/0057461 | A1 | 3/2008 | Cheng et al. |

FOREIGN PATENT DOCUMENTS

| | | | |
|---|---|---|---|
| WO | WO-0180765 A1 * | 11/2001 | ............... A61C 7/00 |
| WO | WO2006/042037 | 4/2006 | |

OTHER PUBLICATIONS

Extended Search Report from European Patent Office on co-pending EP application (19167559.4) dated Aug. 6, 2019.
International Search Report from European Patent Office dated Jul. 23, 2008 for International Application No. PCT/US2007/081262.
Written Opinion from European Patent Office dated Jul. 23, 2008 for International Application No. PCT/US2007/081262.
International Preliminary Reporton Patentability dated Apr. 13, 2010 for International Application No. PCT/US2007/081262.
Office Action from USPTO dated Jul. 16, 2012 for U.S. Appl. No. 12/682,225.
Final Office Action from USPTO dated Feb. 8, 2013 for U.S. Appl. No. 12/682,225.
Office Action from Japanese Patent Office dated May 31, 2013 for Japanese Application No. 2010-528853.
Office Action from USPTO dated Aug. 2, 2013 for U.S. Appl. No. 12/682,225.
Office Action from USPTO dated Sep. 19, 2013 for U.S. Appl. No. 12/682,225.
Notice of Allowance from USPTO dated Apr. 18, 2014 for U.S. Appl. No. 12/682,225.
Office Action from Canadian Intellectual Property Office dated Dec. 18, 2015 for related application CA2,870,360.
Office Action from USPTO dated Dec. 27, 2016 for U.S. Appl. No. 14/461,281.
Communication from European Patent Office dated Apr. 21, 2017 for related European Application No. 07844236.5.
Office Action from USPTO dated Jun. 9, 2017 for U.S. Appl. No. 14/461,281.

* cited by examiner

| OPTION | TREATMENT TYPE | TIME | REDUCTION | AESTHETICS | LINGUAL MOVEMENT |
|---|---|---|---|---|---|
| A | NONE | +++ | +++ | --- | --- |
| B | PROSTHO | ++ | - | -- | --- |
| C | PROSTHO | ++ | -- | 0 | --- |
| D | PROSTHO + ORTHO | + | -- | + | + |
| E | PROSTHO + ORTHO | - | -- | ++ | ++ |
| F | PROSTHO + ORTHO | -- | 0 | +++ | ++ |
| G | ORTHO | -- | +++ | + | ++ |

FIG. 1

OPTION A

OPTION B

OPTION C

OPTION D

OPTION E

OPTION F

OPTION G

PROSTHODONTIC AND ORTHODONTIC APPARATUS AND METHODS

CROSS-REFERENCE TO RELATED APPLICATION

This application is a continuation application of co-pending application Ser. No. 15/700,011, filed Sep. 8, 2017, which is a divisional application of application Ser. No. 14/461,281, filed on Aug. 15, 2014; which is a continuation application of application Ser. No. 12/682,225, filed on Mar. 16, 2011, now U.S. Pat. No. 8,807,999; which is a national phase filing, under 35 U.S.C. § 371(c), of International Application No. PCT/US2007/081262, filed Oct. 12, 2007, the disclosures of which are incorporated herein by reference in their entireties.

BACKGROUND

1. Field of the Invention

The present invention relates to prosthodontic and orthodontic dental procedures.

2. Related Art

Orthodontics is a dental specialty concerned with correcting irregularities in a patient's dentition, such as malocclusion. Orthodontics generally involves the realignment and/or repositioning of a patient's teeth. The corrected alignment and/or position improve the function and appearance of the teeth.

Prosthodontics is a dental specialty concerned with correcting irregularities in a patient's dentition, such as missing, misshaped, malformed, or maloccluded teeth. Whereas orthodontics generally involves realignment and/or repositioning of a patient's teeth, prosthodontics generally involves reshaping a patient's teeth by grinding or cutting and/or building up portions of the teeth with biocompatible dental materials. For example, a prosthodontic procedure may involve the placement of one or more dental restorations, such as crowns, bridges, inlays, and/or veneers. Prosthodontics also corrects for improper tooth color and shape, which orthodontics alone cannot correct.

SUMMARY

The embodiments of the present prosthodontic and orthodontic apparatus and methods have several features, no single one of which is solely responsible for their desirable attributes. Without limiting the scope of the present apparatus and methods as expressed by the claims that follow, their more prominent features will now be discussed briefly. After considering this discussion, and particularly after reading the section entitled "Detailed Description", one will understand how the features of the present embodiments provide advantages, which include the ability to control various restorative parameters during the stages of planning and delivering orthodontic and prosthodontic treatment, the ability to iterate during the planning stages to arrive at various treatment goals and to then select a most desired treatment goal, reduced tooth material removed, preservation of future options for orthodontic and/or prosthodontic procedures, improved prosthodontic outcomes, assisting a dental professional in precisely identifying areas of a patient's dentition to be removed during a prosthodontic procedure, and assisting the dental professional in verifying whether he or she has removed enough tooth material to properly seat dental restorations.

One aspect of the present apparatus and methods includes the realization that in a prosthodontic procedure it is desirable to control restorative parameters so that they fall within desired ranges in the final restorative outcome. A patient typically has one or more goals that he or she wants to achieve through the prosthodontic procedure. By controlling these parameters both during the planning stages and during the delivery of orthodontia/prosthodontia, the patient is more likely to his or her restorative treatment goals.

Another aspect of the present apparatus and methods includes the realization that in a prosthodontic procedure it is desirable to remove as little healthy tooth material as necessary to ensure a structurally sound final restoration. The removal process is irreversible and potentially uncomfortable for the patient. Furthermore, subsequent dental work on the same tooth typically requires further removal of natural tooth structure. Therefore, it is desirable to remove as little natural tooth structure as necessary, since the options for future modifications of the patient's dentition become more limited as more tooth material is eliminated. Excessive removal may also lead to complications, such as creating a need for endodontic treatment (root canal treatment), and compromised retention of the dental restoration.

Another aspect of the present apparatus and methods includes the realization that in a prosthodontic procedure there is a prognosis for each patient based at least in part on the beginning configuration of that patient's dentition. Thus, for patients with severely maloccluded teeth, the restorative prognosis may be poor due at least in part to the severity of the malocclusion. By treating the patient's dentition first with orthodontia prior to performing the prosthodontic procedure, the prognosis for that patient may be significantly improved, because the new tooth positions may require less structural change, and enable more enhanced restorative design.

Another aspect of the present apparatus and methods includes the realization that when placing a preparation guide over a patient's dentition prior to tooth modification, protruding areas of the teeth (areas that are to be removed during the preparation) may prevent the guide from being seated properly unless the areas are actually removed. Thus, it is difficult for the dental professional to identify with precision, areas of the teeth that are to be removed without actually cutting the teeth. It is also difficult for the dental professional to precisely verify whether he or she has removed enough tooth material to properly create the desired dental restoration(s) to be placed. Therefore, it would be advantageous if the dental professional had available a guide that could be used to measure for adequate preparation clearance while at the same time avoiding protruding areas of the patient's teeth that would prevent the guide from being seated properly even in advance of any tooth modification.

BRIEF DESCRIPTION OF THE DRAWINGS

The disclosed embodiments of the present prosthodontic and orthodontic apparatus and methods will now be discussed in detail with an emphasis on highlighting the advantageous features. These embodiments depict the novel and non-obvious apparatus and methods shown in the accompanying drawings, which are for illustrative purposes only. These drawings include the following figures, in which like numerals indicate like parts:

FIG. 1 is a table rating various orthodontic/prosthodontic treatment options against restorative parameters;

DETAILED DESCRIPTION

Figure 2:
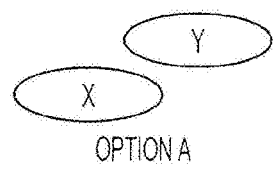
FIG. 2 is a schematic illustration of two teeth in a pretreatment configuration.

It should be understood that the techniques of the present invention may be implemented using a variety of technologies. For example, methods described herein may be implemented in software executing on a computer system, or implemented in hardware using either a combination of microprocessors or other specially designed application specific integrated circuits, programmable logic devices, or various combinations thereof. In particular, methods described herein may be implemented by a series of computer-executable instructions residing on or carried by a suitable computer-readable medium. Suitable computer-readable media may include volatile memory (e.g., RAM) and/or non-volatile memory (e.g., ROM, disk).

Certain embodiments of the present prosthodontic and orthodontic apparatus and methods advantageously combine the benefits of orthodontic treatment with a prosthodontic procedure to enhance the final outcome of the procedure. The embodiments produce a healthy-looking smile with a reduced amount of tooth structure removed as compared to a traditional prosthodontic procedure with no orthodontia. The reduction in tooth structure removed reduces complications that can arise from over-reduction of teeth, such as sensitivity. It also helps to ensure that the reduction may be performed in an accurate, reproducible manner. Further, the options for future modifications of the patient's dentition are increased, since a greater proportion of the patient's original dentition remains after the procedure has been completed.

Certain other embodiments of the present apparatus and methods advantageously enable one or more restorative parameters to be controlled during a prosthodontic procedure. Upon identifying one or more parameters of interest, a dental professional can iterate processes of virtual orthodontia and virtual prosthodontia to observe whether each iteration produces a desired outcome for the parameter(s) of interest. The dental professional may perform the iterations together with the patient. The parameters of interest may include, for example, time of treatment, volume of tooth structure removed, final aesthetics and/or alignment of lingual tooth surfaces or other parameters.

Certain other embodiments of the present apparatus and methods advantageously assist a dental professional in identifying areas of a patient's dentition to be removed during a prosthodontic procedure. The present embodiments also assist the dental professional in verifying whether he or she has removed enough tooth material to properly create dental restoration(s) that are to be placed. The prosthodontic methods described herein may be performed on a patient's entire dentition or on just one tooth. For simplicity, however, some of the present apparatus and methods are shown in the figures with reference to only a single tooth.

Certain other embodiments of the present apparatus and methods advantageously assist a dental professional in forming an orthodontic treatment plan oriented on optimal veneer usage. These embodiments assist the dental professional in quantifying parameters used to properly create dental restoration(s) that are to be placed.

Treatments

Embodiments of the present methods may begin when a patient first consults a dental professional (which may include, but is not limited to, a dentist, an orthodontist, a lab technician, a dental product provider, a dental service provider and the like) regarding an orthodontic procedure and/or a prosthodontic procedure. During the initial consultation, the dental professional and the patient may discuss the patient's treatment goal(s) and any constraints that might limit the range of available treatment options. For example, the patient may desire to have his or her smile enhanced prior to his or her wedding, but the patient may not consult the dental professional until six months prior to the wedding. In such a situation, the timeframe for treatment is limited, and an appropriate orthodontic/prosthodontic treatment plan must be set to fit within the timeframe.

In the table of FIG. 1, the left-hand column lists seven orthodontic/prosthodontic treatment options represented by the letters A-G. Options A-G are schematically illustrated in FIGS. 2-8, which are discussed in detail below. The top row of the table lists four restorative parameters that may be of interest to the patient. The exemplary four restorative parameters are: time required to complete the orthodontic/prosthodontic treatment, reduction in volume of tooth structure resulting from prosthodontic treatment, final aesthetics upon completion of treatment (including teeth color, realistic thickness of teeth and the like), and alignment of lingual tooth surfaces (on tongue side of teeth) upon completion of treatment. As explained in detail below, the table assesses each of the treatment options by assigning qualitative values to each of the restorative parameters for that treatment option. Those of ordinary skill in the art will appreciate that there may be additional restorative parameters not listed in FIG. 1 that may be of interest to some patients. Accordingly, the listed parameters should not be interpreted as limiting the scope of the present embodiments.

In FIG. 1, each of the orthodontic/prosthodontic treatment options is rated against the four listed parameters. To assess a given treatment option, the dental professional and/or patient locates that option in the leftmost column and reads across the table. The symbols appearing in each column indicate whether the treatment option produces a positive outcome or a negative outcome for the parameter of that column. If a treatment option produces a positive outcome for a given parameter, one or more + signs appear in the column for that parameter. If a treatment option produces a negative outcome for a given parameter, one or more – signs appear in the column for that parameter. Multiple + or – signs indicate that that parameter is particularly positive or particularly negative for that treatment option. If a 0 appears in a column, then that parameter is considered neutral with respect to that treatment option.

FIG. 2 schematically illustrates a first tooth X and a second tooth Y in a pretreatment configuration, while FIGS. 3-8 illustrate the same teeth in various post-treatment configurations. In FIGS. 2-8, the illustrated teeth are molars, and the cuspal (chewing) surface of each molar faces the viewer. The lingual (tongue side) surface of each tooth faces downward, and the buccal (opposite the tongue side) surface of each tooth faces upward.

In the pretreatment configuration of FIG. 2, tooth X is positioned closer to the tongue than tooth Y. Thus, neither the lingual surfaces nor the buccal surfaces of the teeth are aligned. Further, a portion of tooth Y is overlapping a portion of tooth X. Thus, to align the lingual and buccal surfaces of the teeth, either the teeth must first be moved away from each other, or the overlapping portions of one or both teeth must be removed.

FIG. 1 includes option A, which represents no orthodontic or prosthodontic treatment and provides a baseline from which to relatively measure other outcomes. Thus, the teeth remain as they appear in FIG. 2. Referring to the table in FIG. 1 and reading across the first row, option A produces a very strongly positive outcome (+++) for the time required to complete the treatment, because there is no treatment. Option A also produces a very strongly positive outcome (+++) for reduction in volume of tooth structure, because no tooth structure is removed. Finally, treatment option A produces strongly negative outcomes (---) for both final aesthetics and alignment of lingual tooth surfaces, because no improvements are made in these areas.

Figure 3:
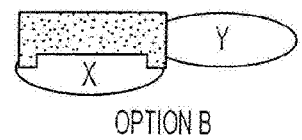
FIG. 3 is a schematic illustration of the teeth of FIG. 2 in a post-treatment configuration according to one example prosthodontic treatment plan.

FIG. 3 schematically illustrates one treatment plan that involves only prosthodontics. To transform the teeth from the configuration of FIG. 2 into the configuration of FIG. 3, the overlapping portion of tooth Y is cut or ground away, and a veneer is applied to the buccal surface of tooth X. In order to firmly secure the veneer to the tooth, small portions on either side of tooth X are removed to form butt joints with the veneer.

Referring to the table in FIG. 1 and reading across the second row, treatment option B produces a strongly positive outcome (++) for the time required to complete the treatment, because the treatment involves only prosthodontia, which may be completed in a much shorter timeframe than orthodontia. However, treatment option B produces a negative outcome (–) for reduction in volume of tooth structure, since the overlapping portion of tooth Y is removed and small portions on either side of the tooth X are removed to form the butt joints. Treatment option B produces a more negative outcome (––) for final aesthetics, since a very thick veneer is added to tooth X, and since there is no matching veneer added to tooth Y. Thus, the color of tooth Y is not improved, and there may be some color contrast between the buccal surfaces of teeth X and Y. Finally, treatment option B produces a very strong negative outcome (---) for alignment of lingual tooth surfaces, the misalignment of the lingual surfaces is not corrected at all.

Figure 4:
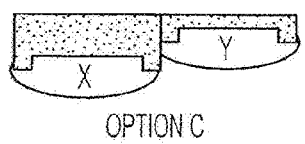
FIG. 4 is a schematic illustration of the teeth of FIG. 2 in a post-treatment configuration according to another example prosthodontic treatment plan.

FIG. 4 schematically illustrates another treatment plan that also involves only prosthodontics. To transform the teeth from the configuration of FIG. 2 into the configuration of FIG. 4, the overlapping portion of tooth Y is ground away, and a veneer is applied to the buccal surface of tooth X. In this embodiment, a veneer is also applied to the buccal surface of tooth Y. As in treatment option B above, small portions on either side of tooth X are removed to form butt joints with the veneer. To secure the veneer to tooth Y, a thin wall of the buccal surface of tooth Y is removed in addition to small portions on either side of tooth Y for butt joints.

Referring to the table in FIG. 1 and reading across the third row, treatment option C produces a strong positive outcome (++) for the time required to complete the treatment, because the treatment involves only prosthodontia. Treatment option C produces a strong negative outcome (––) for reduction in volume of tooth structure, because not only is the overlapping tooth structure of tooth Y removed, but tooth structure is removed from tooth X and tooth Y to form butt joints and to make room for the veneer on tooth Y. Treatment option C produces a neutral outcome (0) for final aesthetics, because although there is a very thick veneer added tooth X, the color of both teeth are improved because of the matching veneers. Finally, like treatment option B treatment option C also produces a very strong negative outcome (---) for alignment of lingual tooth surfaces.

In order to arrive at the best possible outcome for a patient's specific condition or treatment requirements, trade-offs may be made between each of the restorative parameters. It is apparent that for some situations where, for example, aesthetics and lingual alignment are important parameters, and particularly where it is desired to minimize the amount of tooth reduction, some combination of orthodontics and prosthodontics may be indicated.

Figure 5:
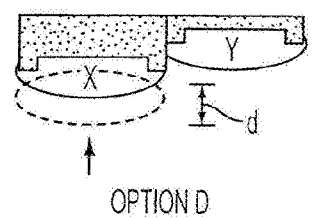
FIG. 5 is a schematic illustration of the teeth of FIG. 2 in a post-treatment configuration according to one example orthodontic/prosthodontic treatment plan.

FIG. 5 schematically illustrates another treatment plan that involves both orthodontics and prosthodontics. To transform the teeth from the configuration of FIG. 2 into the configuration of FIG. 5, the overlapping portion of tooth Y is ground away, and tooth X is moved forward (away from the tongue). However, tooth X is only moved forward through the distance d, such that while alignment of the buccal and lingual surfaces of the teeth is improved, it is not made perfect. In treatment option D veneers are also applied to the buccal surfaces of teeth X and Y.

Referring to the table in FIG. 1 and reading across the fourth row, treatment option D produces a positive outcome (+) for the time required to complete the treatment, because although the treatment involves orthodontia, the treatment nevertheless takes less time than a treatment option that involves more movement of tooth X. Treatment option D produces strong negative outcome (--) for reduction in volume of tooth structure, because not only is the overlapping tooth structure of tooth Y removed, but tooth structure is removed from tooth X and tooth Y to form butt joints and to make room for the veneer on tooth Y. Treatment option D produces a positive outcome (+) for final aesthetics, since, due to the movement of tooth X, relatively thin veneers are added to both teeth. Finally, treatment option D produces a positive outcome (+) for alignment of lingual tooth surfaces, because the alignment is improved over that of the pretreatment configuration.

Figure 6:
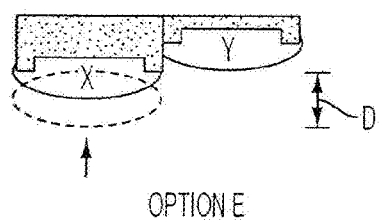
FIG. 6 is a schematic illustration of the teeth of FIG. 2 in a post-treatment configuration according to another example orthodontic/prosthodontic treatment plan.

FIG. 6 schematically illustrates another treatment plan that also involves both orthodontics and prosthodontics. To transform the teeth from the configuration of FIG. 2 into the configuration of FIG. 6, the overlapping portion of tooth Y is ground away, and tooth X is moved forward (away from the tongue). In contrast to treatment option D, tooth X is moved forward through the distance D until the lingual surfaces of the teeth align. In treatment option E, veneers are also applied to the buccal surfaces of teeth X and Y.

Referring to the table in FIG. 1 and reading across the fifth row, treatment option E produces a negative outcome (-) for the time required to complete the treatment, because the treatment involves orthodontia to move tooth X through a greater distance D when compared to other treatment options. Treatment option E produces a strong negative outcome (--) for reduction in volume of tooth structure, because not only is the overlapping tooth structure of tooth Y removed, but tooth structure is removed from tooth X and tooth Y to form butt joints and to make room for veneers on both tooth X and tooth Y. Treatment option E produces a strong positive outcome (++) for final aesthetics, because thin veneers are added to both teeth and both teeth appear to be of normal thickness. Finally, treatment option E produces a strongly positive outcome (++) for alignment of lingual tooth surfaces, because the alignment is greatly improved over that of the pretreatment configuration.

Figure 7:
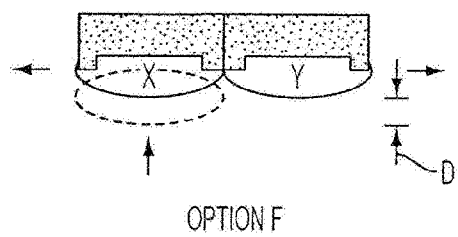
FIG. 7 is a schematic illustration of the teeth of FIG. 2 in a post-treatment configuration according to another example orthodontic/prosthodontic treatment plan.

FIG. 7 schematically illustrates another treatment plan that involves orthodontics and prosthodontics. To transform the teeth from the configuration of FIG. 2 into the configuration of FIG. 7, the teeth are moved away from one another (as represented by the oppositely directed arrows on either side of the teeth) and tooth X is moved forward (away from the tongue) through the distance D until the buccal and lingual surfaces of the teeth align. However after the teeth are moved, treatment option F includes adding veneers to the buccal surfaces of tooth X and tooth Y.

Referring to the table in FIG. 1 and reading across the sixth row, treatment option F produces a strong negative outcome (--) for the time required to complete the treatment, because the treatment involves orthodontia to move tooth X through a distance D and to move tooth X away from tooth Y. Treatment option F produces a very neutral outcome (0) for reduction in volume of tooth structure, because only a small amount of tooth structure is removed on from tooth X and tooth Y to form butt joins for the veneers. Treatment option F produces a very strong positive outcome (+++) for final aesthetics because the teeth are properly aligned, the teeth appear to be of normal thickness and the veneers correct any discoloration or misshapenness from the pretreatment configuration. Finally, treatment option F produces a strong positive outcome (++) for alignment of lingual tooth surfaces, because the alignment is greatly improved over that of the pretreatment configuration.

Figure 8:
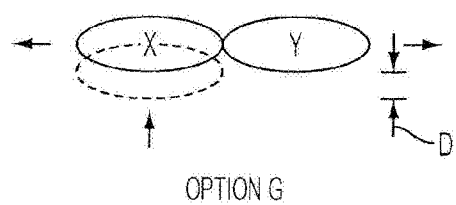
FIG. 8 is a schematic illustration of the teeth of FIG. 2 in a post-treatment configuration according to one example orthodontic treatment plan.

FIG. 8 schematically illustrates another treatment plan that involves only orthodontics. To transform the teeth from the configuration of FIG. 2 into the configuration of FIG. 8, the teeth are moved away from one another (as represented by the oppositely directed arrows on either side of the teeth) and tooth X is moved forward (away from the tongue) through the distance D until the buccal and lingual surfaces of the teeth align.

Referring to the table in FIG. 1 and reading across the seventh row, treatment option G produces a strong negative outcome (--) for the time required to complete the treatment, because the treatment involves orthodontia to move tooth X through a distance D and to move tooth X away from tooth Y. Treatment option G produces a very strong positive outcome (+++) for reduction in volume of tooth structure, because no tooth structure is removed. Treatment option G produces a positive outcome (+) for final aesthetics because the teeth are properly aligned and appear to be of normal thickness. However, because no veneers are added to the teeth, any discoloration or misshapenness from the pretreatment configuration remains. Finally, treatment option G produces a strong positive outcome (++) for alignment of lingual tooth surfaces, because the alignment is greatly improved over that of the pretreatment configuration.

While the examples described with respect to FIGS. 2-8 relate to two teeth, similar principals apply to other configurations of maloccluded and misshapen teeth and apply to patient with two or more maloccluded teeth.

After the initial consultation between the patient and the dental professional, the dental professional and the patient may develop an orthodontic treatment plan and/or a prosthodontic treatment plan. The orthodontic treatment plan may transform the patient's dentition from its beginning configuration to an intermediate configuration, and the prosthodontic treatment plan may transform the patient's dentition from the intermediate configuration to a final configuration. The intermediate configuration may also be referred to as an orthodontic treatment goal, and the final configuration may also be referred to as a restorative treatment goal.

Figure 9:
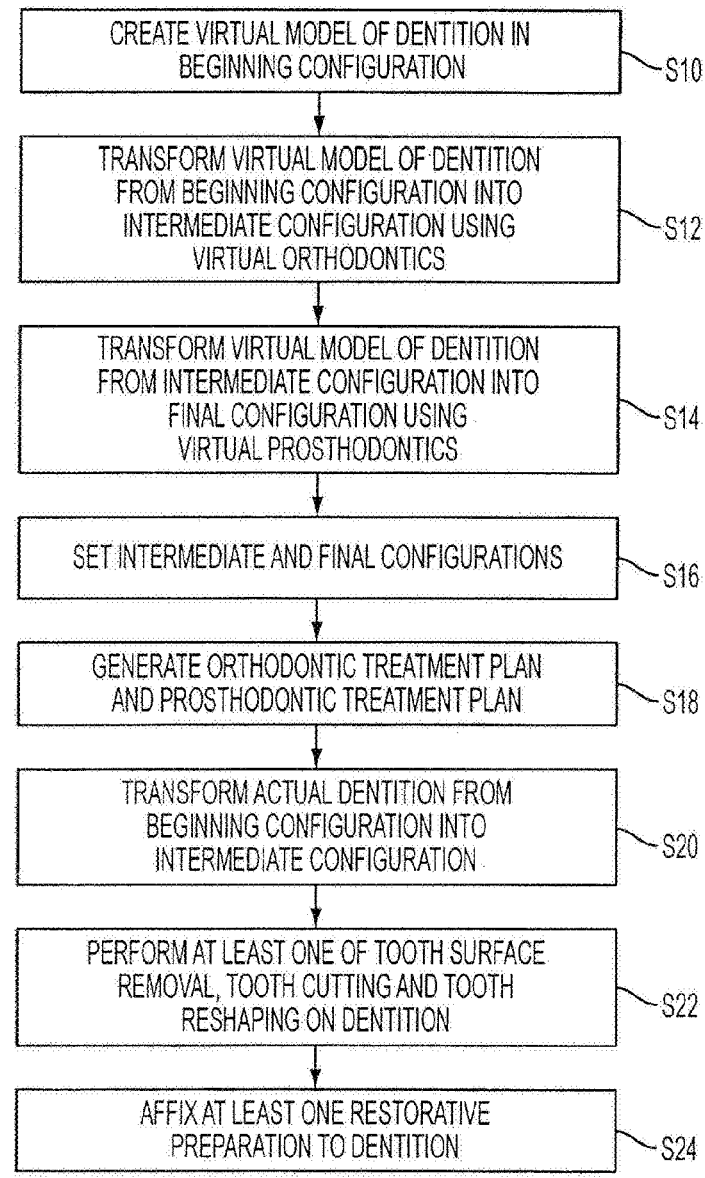
FIG. 9 is a flowchart illustrating steps that may be performed in certain embodiments of the present methods.

With reference to FIG. 9, a computer-generated, three-dimensional, virtual model of the patient's dentition in the beginning configuration is created, as shown at step S10. Unlike some 3-D educational software which show representative "typodont" models for illustrative purposes, this model represents the patient's actual dentition in a beginning configuration. The virtual model may be generated prior to any tooth preparation, so that the model represents the patient's dentition in a pretreatment state. Some processes for making such a virtual model are described in, for example, U.S. Patent Application Publication No. US 2006/0154207, published on Jul. 13, 2006 and in U.S. patent application Ser. No. 11/678,749, filed on Feb. 26, 2007 by Kaza et al. The entire disclosures of the '207 publication and the '749 application are hereby incorporated herein by reference.

With continued reference to FIG. 9, the virtual model of the beginning configuration using virtual orthodontia may be transformed to create a computer-generated, three-dimensional, virtual model of the patient's dentition in an intermediate configuration, as shown at step SI2. The virtual orthodontia may include manipulation and movement of teeth in the virtual model. The virtual model of the intermediate configuration may be transformed using virtual prosthodontia to create a computer-generated, three-dimensional, virtual model of the patient's dentition in a desired final configuration, as shown at step S14. The virtual prosthodontics may include one or more modifications of the virtual model, such as tooth mass removal or build-up and/or the placement of one or more dental restorations. Those of ordinary skill in the art will appreciate that steps S12 and S14 may be performed in any order, and may even be performed simultaneously. In addition, steps S12 and S14 may be iterated upon. During each iterative step, the final model may be evaluated and iterated again or finalized into a treatment plan. These iterative steps are described in greater detail below with respect to FIG. 11.

Finalizing a treatment plan may include setting the intermediate and final configurations, as shown at step S16 in FIG. 9. Once these configurations are set, the orthodontic treatment plan and the prosthodontic treatment plan are generated, as shown at step SI8. The orthodontic treatment plan may transform the dentition from the beginning configuration to the intermediate configuration, and the prosthodontic treatment plan will transform the dentition from the intermediate configuration to the final configuration or restorative treatment goal.

Figure 10:
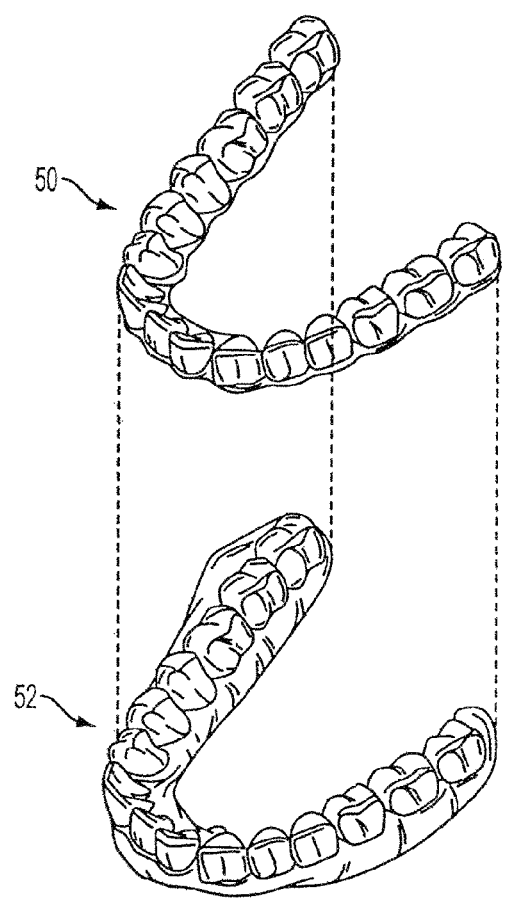
FIG. 10 is a perspective view of one embodiment of an aligner that may be used in connection with certain embodiments of the present apparatus and methods.

Once the treatment plan is finalized, the next step in the present method may be to deliver a course of orthodontic treatment according to the orthodontic treatment plan, as shown at step S20 in FIG. 9. The orthodontia may proceed using any well-known apparatus and methods, such as orthodontic brackets and wires (braces). Alternatively, or in addition, the orthodontia may include a series of plastic orthodontic appliances or aligners. FIG. 10 illustrates one such aligner 50 that is adapted to fit over a patient's lower arch 52. The aligners, each of which may be a polymeric shell having a teeth-receiving cavity, are described in detail in the '893 patent and the '807 patent, both of which are incorporated herein by reference above. The patient wears the series of aligners in order to achieve incremental repositioning of individual teeth in his or her jaw.

The polymeric aligner 50 of FIG. 10 may be formed from a thin sheet of a suitable elastomeric polymer, such as Tru-Tain 0.030" thermal forming dental material, available from Tru-Tain Plastics of Rochester, Minn. Other aligner materials can include, but are not limited to polyester, polyurethane, polypropylene, polycarbonate, poly-blend, and poly-laminates. Usually, no wires or other structures are provided for holding the aligner in place over the teeth, though it may be possible to incorporate auxiliary devices such as wires, hooks, and elastics into the aligners to assist in appliance retention. It is also possible to provide individual anchor attachments directly on the teeth, with corresponding receptacles or apertures in the aligner so that the aligner can apply either a retentive or a supplemental force on the tooth that would not be possible in the absence of such an anchor.

The aligners are generated using data representing the patient's teeth. The data may be from scans of dental impressions, dental casts, and/or direct scans of the patient. Each polymeric shell may be configured so that its tooth-receiving cavity has a geometry corresponding to an incremental tooth arrangement intended for the patient. The patient's teeth are repositioned from their initial arrangement to the next incremental arrangement by placing the aligners sequentially over the teeth. The patient wears each aligner until the teeth have conformed to the position defined by the aligner. At that point, the patient moves onto the next aligner stage of the planned course of treatment and replaces the old aligner with the next aligner in the series until the intended treatment outcome is achieved. The course of treatment may require a recalibration scan and additional aligners if the teeth do not exactly track according to the design within the aligner. However, because the aligners are removable and not bonded to the teeth, the process is convenient and hygienic for the patient, generally more so than traditional braces, which are affixed directly to the teeth and not intended to be removed by the patient during the course of treatment.

The polymeric shell can fit over any and typically all teeth present in the upper or lower jaw. Often, only a select few of the teeth are repositioned at a given time while remaining teeth provide a base or an anchor region for holding the aligner in place as the aligner applies a repositioning force against the tooth or teeth to be repositioned. In many cases, all teeth may be repositioned at some point during the treatment. In such cases, the moved teeth may also serve as a base or anchor region for holding the aligner.

Upon completion of the orthodontic treatment plan, a dental professional may perform one or more prosthodontic procedures according to the prosthodontic treatment plan. As part of the prosthodontic procedure(s), the dental professional prepares the necessary teeth by reducing the tooth surfaces as needed to ensure proper retention, strength, and aesthetics for the final restoration. The prepared teeth may require one or more provisional restorations. In some situations, however, the final restoration(s) may be immediately fabricated in the dental professional's office and placed without the need for any provisionals. An example of an immediate fabrication system is the Siriona CEREC™ milling machine, which uses an in-office scan of the prepared dentition, the creation of a virtual restoration over the preparation scan, and the milling of a porcelain block according to the virtual restoration in consideration of the preparation scan.

Prior to placing the dental restoration(s) on the patient's dentition, at least one of tooth surface removal, cutting and/or reshaping may be performed, as shown in step S22 in FIG. 9. The removal/cutting/reshaping prepares the dentition to receive the dental restoration(s). As discussed above, such preparation generally involves the removal of at least a portion of a tooth, its enamel and/or dentin, and some or all pre-existing restorations on the tooth. The reshaping may also involve building up some areas of the dentition using biocompatible materials such as composite, fiberglass, carbon fiber, gold, amalgam, titanium, and/or stainless steel. When removing tooth material to accommodate a dental restoration, generally 1 mm of tooth material is removed to ensure adequate restoration strength and desired aesthetics. However, as those of ordinary skill in the art will appreciate more or less tooth material may be removed.

During the steps of removal/cutting/reshaping, the accuracy and design of the removal, cutting and/or reshaping may be periodically verified. In one embodiment, one or more preparation guides may be positioned over the patient's dentition. The preparation guide, which resembles an aligner and is typically manufactured in a similar way, may embody the final restorative configuration. Clearances between teeth surfaces and the preparation guide may be measured to verify that the desired amounts of tooth surface have been removed. To determine whether adequate tooth material has been removed, the guide may be seated on the teeth and any interference between the tooth and the guide may be removed. Once the guide is fully seated, the clearances between the guide and the teeth are checked and additional tooth material is removed until adequate clearances are achieved between the inner surfaces of the guide and the surfaces of the teeth receiving the final restoration(s).

After the desired amount of tooth material has been removed in conjunction with the preparation guide, a provisional or final restoration may be prepared and affixed on the patient's dentition, as shown in step S24 in FIG. 9. An adhesive, such as dental cement, may be used to affix the restoration on the teeth to prevent it from leaking and/or dislodging.

As described above, in the foregoing methods at least some of the steps may be performed in an iterative fashion, and may include one or more sub-steps. The iteration enables a dental professional and a patient to focus on one or more restorative parameters that are of interest to the patient, and to control the outcome of the treatment with respect to these parameters. Therefore, prior to or during the present methods the dental professional and the patient may identify one or more restorative parameters that are of interest to the patient. As discussed above with respect to FIG. 1, these parameters may include: treatment time, volume of tooth structure removed, final aesthetics and/or alignment of lingual tooth surfaces. Moreover, after creating a virtual model of the patient's dentition in the beginning configuration (step S10, FIG. 11), the dental professional may transform the virtual model to create virtual models representing the desired intermediate configuration (SI2) and final configuration (SI4). In addition, at step S26 the dental professional may evaluate the one or more restorative parameters of interest, and then iterate the movement steps and again evaluate the restorative parameter(s). The dental professional and the patient may repeat these iterative steps until the restorative parameter(s) fall within desired ranges. Again, those of ordinary skill in the art will appreciate that the iterative steps outlined above may be performed in any order.

In step S26, the evaluation step may focus on the total volume of tooth structure removed in order to reach the final configuration. The evaluation may be based on, for example, a desired threshold of the total volume of tooth structure. For example, the dental professional may begin by superimposing the dentition in the intermediate configuration and the dentition in the final configuration to identify on the superimposed models the intersection boundaries at the areas where the dentition of the intermediate configuration protrudes beyond the dentition of the final configuration. Using the three-dimensional geometrical models, the volume of the protruding tooth structure may be calculated. The volume of the protruding dentition represents the volume of tooth structure that may be removed by the dental professional during the prosthodontic procedure.

As a result of the evaluation and visualization, the dental professional, perhaps after consulting the patient, may modify the orthodontic treatment plan by moving and aligning the teeth using virtual orthodontics into a configuration that varies from the orthodontic treatment goal. The dental professional may also modify the prosthodontic treatment plan by modifying the teeth using virtual prosthodontics into a configuration that varies from the restorative treatment goal. The dental professional may repeat these steps several times. In addition, or in the alternative, as a result of the evaluation and visualization, the dental professional may modify the orthodontic treatment goal and/or the restorative treatment goal. For example, the dental professional may modify the restorative treatment goal by modifying the desired final tooth position goal and/or tooth shape goal.

In step S26 the dental professional may superimpose the modified models to determine the impact of the modifications on the volume of tooth structure that extends outward from the intersection boundaries. The dental professional may continue to modify the virtual representations of the tooth structures in both the virtual orthodontic plan and virtual restorative goal models until the dental professional has iteratively arrived at an acceptable preparation design that provides for a desired threshold value of the parameters of interest. In the present invention, the threshold value represents either a maximum, or if appropriate, a minimum condition that the dental professional determines is an acceptable variation to any given restorative parameter. For example, the dental professional may set a threshold value that represents the maximum amount of the total volume of the tooth structure to be removed to create the final tooth configuration. A threshold value may also be, for example, the maximum amount of time available for treatment or the maximum thickness of a veneer to be placed on a tooth.

The ability to virtually iterate the preparation specifications as applied to the virtual beginning model of the dentition as provided in steps S12 and S14 provides the dental professional the ability to modify the preparation design prior to any actual moving or cutting of the teeth. In addition, the dental professional may also visualize the impact of the preparation to the actual tooth, for example, in terms of volume of tooth material removed, the different areas of tooth affected, and the depth of the preparation, which is advantageous for avoiding sensitivity or other treatments, such as root canals.

Once the dental professional has arrived at a preparation design that meets desired thresholds for the restorative parameters of interest, then the dental professional may set the intermediate and final configurations, as shown at step S28. The dental professional may then map out the orthodontic and prosthodontic treatment plans based upon the beginning, intermediate and final configurations, as shown at step S30.

Using the orthodontic and prosthodontic treatment plans, the dental professional may next create, or have created, orthodontic appliances and restorative preparations, as shown at step S32. Steps S20, S22 and S24 may then proceed as shown in FIG. 11 and as described above with respect to FIG. 9.

Figure 11:
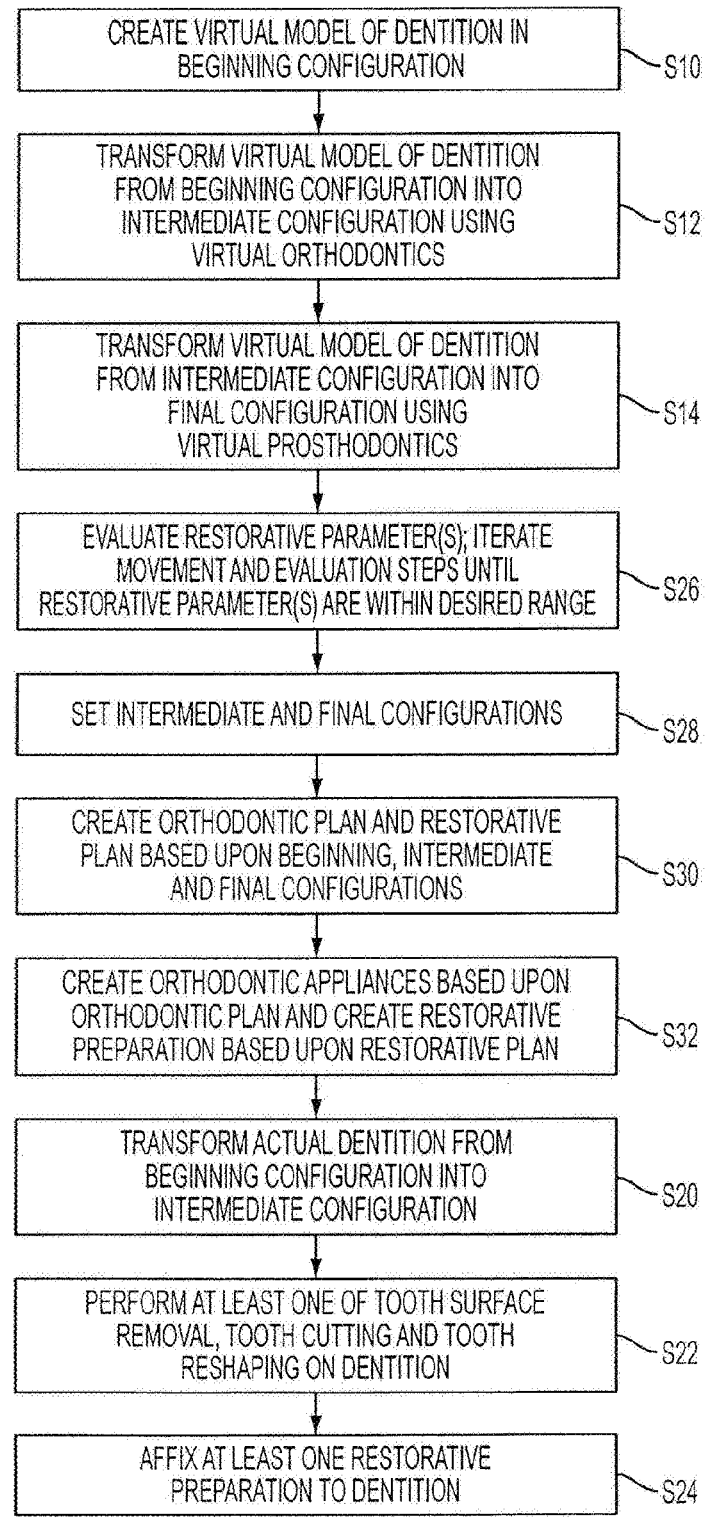
FIG. 11 is a flowchart illustrating steps that may be performed in certain embodiments of the present methods.

Many of the various embodiments included in the method steps described with reference to FIGS. 9 and 11 are illustrated in the following example.

In accordance with one embodiment of the present methods, a dental professional may begin a restorative procedure, by first meeting with a patient to determine which of the restorative factors available are achievable to the degree desired by the patient given the patient's treatment priorities. For example, the patient may present to the dentist having a malocclusion like that shown in FIG. 2. In this example, the patient may explain to the dentist that she is anticipating a wedding day that is only six months in the future. The bride-to-be wants her teeth (tooth X and Y, in this example) to appear as white and as straight as possible, but she is not concerned with the lingual surface of her teeth as it does not bother her in its present condition. The dental professional notes that the patient has relatively unhealthy teeth and thus determines that the degree of tooth volume reduction, if needed, should be minimized.

The dental professional may apprise the patient with her options, while referring to the table in FIG. 1. Of the options available, the dental professional mentions that Options B and C provide the best desired outcome regarding time of treatment in keeping with the patient's six-month timeframe. However, the dental professional may explain that Option B is not as aesthetically desirable as Option C, since Option B does not provide for a matching veneer between the subject teeth. The dental professional may also explain that Options B and C require a relatively thick veneer be placed on one of the subject teeth to create the illusion that the buccal surface of the teeth are properly aligned.

The patient reviews Options B and C and determines that Options C provides a semi-satisfactory solution, but that the thick veneer is problematic for her. The dental professional may then suggest that the thickness of the veneer may be reduced by moving the subject teeth first, as in Option D. The patient asks to visualize the anticipated results.

To begin, the dental professional scans or photographs the patient's actual dentition to create the virtual model and inputs the data into a computer running the modeling software.

The dental professional may then manipulate the virtual beginning model using the computer software, to simulate the effect of orthodontic treatment by virtually repositioning the subject teeth, tooth X and tooth Y, into a different position. In this example, the dental professional determines that to expedite tooth movement, the portion of tooth Y that overlaps tooth X is to be removed.

Using the software model, the dental professional may quantify a distance dj (FIG. 5) that may be achieved in the prescribed timeframe (e.g. 6 months), which requires a certain amount of tooth volume reduction Vi, and yields a veneer thickness Tj. The dental professional may then manipulate the tooth X and tooth Y again to generate a distance 62 that may be achieved in the prescribed timeframe, which requires an amount of tooth volume reduction V2 and yield a veneer thickness T2 and so on until the dental professional decides that he has generated a number of suitable options ($d_{1 \ldots n}$, $V_{1 \ldots n}$, $T_{1 \ldots n}$) for the patient to review. Since the dental professional is concerned with the amount of tooth volume reduction, the dental professional may set a threshold value for the amount of tooth volume reduction ($V_1, V_2 \ldots V_n$) that he has determined is tolerable for this patient.

Next, the dental professional, in consultation with the patient, may review the options and visualize the results, to determine, which provides a reduction to the thickness of the veneer to the patient's satisfaction. If the patient is satisfied, and the dental professional and the patient have agreed upon the desired final configuration for the dentition, the dental professional may then use the computer software to create a suitable prescription for moving the patient's teeth.

In the above example, before finalizing the prescription, the patient informs the dental professional that her wedding plans have been canceled, but that she still desires to have her teeth restored within the next 12 months. The dental professional explains that, since there is more time available for an orthodontic procedure, the patient has more options to choose from with regard to the restoration, for example, Options E, F, and G of FIG. 1.

The dental professional then revisits the virtual model of the patient's dentition and again begins to manipulate the teeth to determine, as before, which Options now provide the patient with the most suitable outcome given the new timeframe.

Preparation Guides

Although not shown in FIG. 11, the treatment plans could also be used to create preparation guides or templates to help in the restorative aspect of tooth preparation, temporary restoration creation and creation of virtual wax-ups and possible final veneers. An example of a preparation guide that could be created using the treatment plans is discussed below with reference to FIGS. 12-19.

Figure 12:
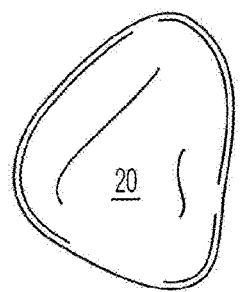
FIG. 12 is a front elevation view of a tooth in a beginning configuration.

FIG. 12 illustrates a tooth 20 in a beginning configuration, prior to any prosthodontic modifications. In accordance with one embodiment of the present methods, a dental professional may begin a prosthodontic procedure by creating a first virtual model of a patient's dentition in a beginning configuration, as shown at step SI00 in FIG. 19. The virtual model may be generated by digitally scanning and/or photographing the actual dentition and inputting the data into a computer running modeling software. The dental professional may store the beginning model for use in a comparison, as described below.

The dental professional may then manipulate the virtual beginning model using the computer software, as shown at step SI02. This manipulation may include simulating the effect of orthodontic treatment by virtually repositioning one or more teeth into a different position, such that the amount of tooth reduction necessary becomes reduced or more balanced for the desired restorative outcome. On the computer screen, the dental professional may also remove portions of the teeth and/or build-up other portions of the teeth in order to generate a second virtual model of the patient's dentition in a desired final configuration (SI02). After consultation with the patient (SI04), the dental professional may perform additional modifications to the second virtual model (S106) until the dental professional and the patient agree on the desired final configuration.

Figure 13:
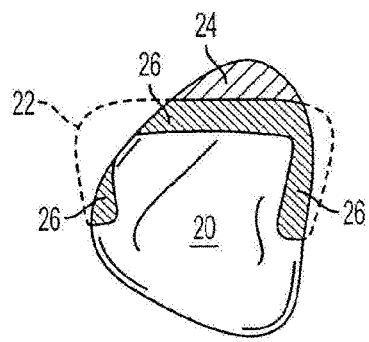
FIG. 13 is a front elevation view of the tooth of FIG. 12 superimposed with a desired final configuration for the tooth, according to one embodiment of the present methods.

FIG. 13 illustrates one example of tooth modifications with which the dental professional may experiment, and about which the dental professional and the patient may confer. In FIG. 13, the tooth 20 is shown in the beginning configuration (solid lines) and in one possible final configuration (dashed lines). To reach the final configuration the dental professional applies a dental restoration to the tooth 20. In the illustrated embodiment, the dental restoration is a veneer 22. However, those of ordinary skill in the art will appreciate that the present methods may involve the placement of any type of dental restoration, such as a bridge or a crown. Before placing the veneer 22 on the tooth 20, the dental professional prepares the tooth 20 by removing some surface material. For example, the dental professional may need to completely cut off a portion 24 (upper shaded portion) of the tooth 20 that would extend past the veneer 22. In other areas 26 (lower shaded portions) the dental professional may need to remove just a portion of the tooth surface (generally about 1 mm) in order to create room for the veneer.

Figure 14:
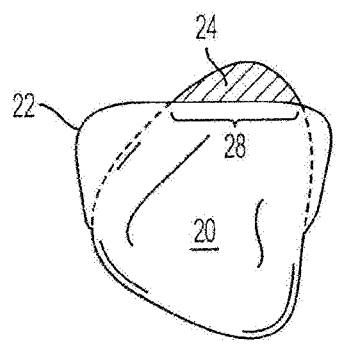
FIG. 14 is a front elevation view of the tooth of FIG. 12 superimposed with a desired final configuration for the tooth, according to one embodiment of the present methods.
Figure 19:
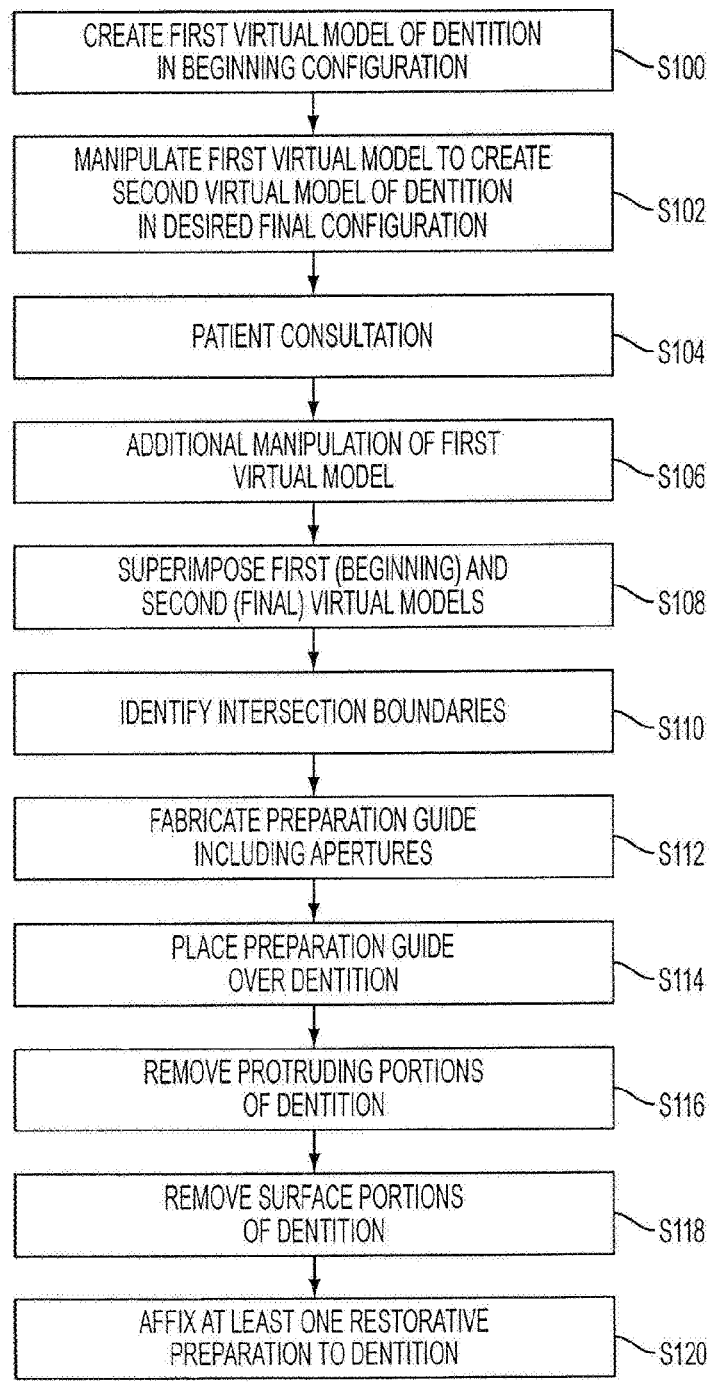
FIG. 19 is a flowchart illustrating steps in another embodiment of the present methods.

Once the dental professional and the patient have agreed upon the desired final configuration for the dentition, the dental professional may then use the computer software to superimpose the first (beginning) and second (final) virtual models, as shown at step SI08 in FIG. 19. For example, FIG. 14 illustrates a model of a final configuration including the veneer 22 superimposed over a model of the actual configuration of the tooth 20. In the superimposed models, the portion 24 of the beginning dentition protrudes beyond the veneer 22. The dental professional will remove the protruding portion 24 from the patient's actual dentition during the prosthodontic procedure.

To enhance the precision with which he or she removes protruding portions of the patient's dentition, the dental professional may use the superimposed models to generate a preparation guide that emphasizes the protruding portions. The preparation guide may be an overlay that substantially conforms to the second dentition model, but includes apertures that enable protruding portions of the actual dentition to extend beyond the overlay so that they do not interfere with the proper seating of the overlay upon the dentition.

To generate the overlay, the dental professional may begin by identifying on the superimposed models the intersection boundaries at the areas where the dentition of the first model protrudes beyond the dentition of the second model, as shown at step SI 10 in FIG. 19. For example, FIG. 14 illustrates one intersection boundary 28 between the tooth 20 and the veneer 22. The modeling software may be programmed to identify these boundaries and to highlight them for the dental professional. The portion 24 of the dentition that extends outward from the intersection boundary 28 will be removed by the dental professional during the prosthodontic procedure.

Figure 15:
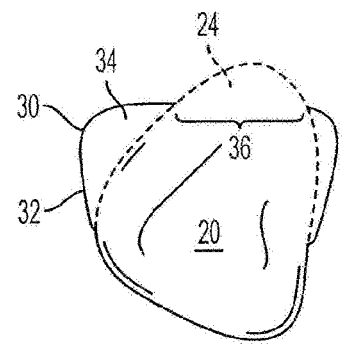
FIG. 15 is a front elevation view of the tooth of FIG. 12 and one embodiment of the present prosthodontic apparatus.

Once the intersection boundaries have been identified, a preparation guide may be fabricated that substantially conforms to the second model but includes apertures defined by the intersection boundaries, as shown at step SI 12 in FIG. 19. An example of a preparation guide or overlay 30, for a single tooth 20 is illustrated in FIG. 15. The overlay 30 includes a wall portion 32 forming a cavity 34 configured to receive the tooth 20. The preparation guide 30 includes an aperture 36 that corresponds to the intersection boundary 28 shown in FIG. 14. The apertures 36 allow the protruding portions 24 of the tooth 20, to extend through the aperture 36. The protruding portions 24 thus to not interfere with proper seating of the guide 30 upon the tooth 20 in the configuration prior to removal of any tooth material. Guide 30 may be placed over tooth 20 to quickly and efficiently identify protruding portions 24 that are to be removed.

Figure 16:
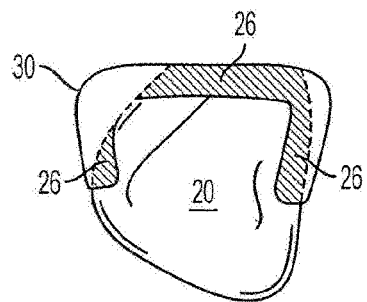
FIG. 16 is a front elevation view of the tooth of FIG. 12 and one embodiment of the present prosthodontic apparatus, illustrating the step of removing a portion of the tooth that extends beyond the apparatus.

After placing the preparation guide 30 over the tooth 20 (step SI 14 in FIG. 19), the dental professional removes the protruding portion 24 (step SI 16). FIG. 16 illustrates the tooth 20 after removal of the protruding portion and with the preparation guide 30 still in place. Using the guide 30 over the tooth 20 as shown, the dental professional can remove the protruding portion of the tooth 20 with greater precision as compared to a procedure involving no overlay. The dental professional simply cuts or grinds down any portions of the tooth 20 that extend beyond the overlay 30. The overlay 30 thus not only highlights the portions of the tooth 20 to be removed, but it also shields portions of the tooth 20 that are not to be removed, thereby preventing unnecessary tooth reduction.

Figure 17:
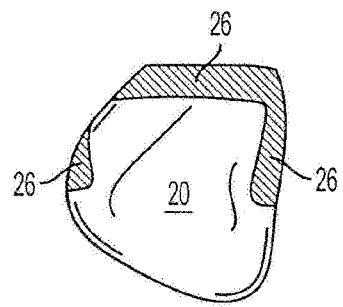
FIG. 17 is a front elevation view of the tooth of FIG. 12 after it has been prepared according to one embodiment of the present methods.
Figure 18:
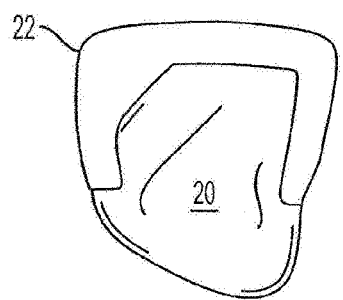
FIG. 18 is a front elevation view of the tooth of FIG. 12 and a dental restoration placed in accordance with one embodiment of the present methods.

If a dental restoration 22 is to be placed over the tooth 20, the dental professional also removes portions 26 of the tooth 20 in order to create space for the veneer 22, as shown in FIG. 16 and at step SI 18 in FIG. 19. The dental professional may use the guide 30 to ensure that the removed tooth portions provide adequate thickness for the veneer 22. For example, the dental professional may place the guide 30 over the tooth 20 as shown in FIG. 16, perforate the guide 30, and measure with a probe the distances between the tooth 20 and the inner surfaces of the guide 30. When the tooth 20 has been fully prepared, as shown in FIG. 17, the dental professional applies the veneer 22, as shown in FIG. 18 and at step SI20 in FIG. 19.

The guide 30 may be fabricated using any well known method or suitable technique, for example, a rapid prototyping method or a molding technique. During the fabrication process, the apertures 36 in the guide 30 may be produced as the guide 30 is formed, or they may be cut out of the guide 30 after it has been formed.

A given guide may include just one aperture or a plurality of apertures. The boundaries of the aperture(s) may be electronically determined and the locations provided to cutting machinery to remove material at the aperture locations. Alternatively, the borders of the aperture(s) may be marked on the guide during the fabrication process so the dental professional may cut out the material at the aperture locations himself. The marking may be performed using ink and/or laser marking, for example.

Those of ordinary skill in the art will appreciate that the guide 30 described above may be used in conjunction with any of the methods described above. For example, the guide 30 may be employed during step S22 shown in FIGS. 8 and 10. Alternatively, the guide 30 may be used in other methods not disclosed herein. When used in conjunction with a method including an orthodontic treatment plan and a prosthodontic treatment plan, such as certain embodiments of the methods described above, the dental professional may construct the guide 30 by superimposing the virtual model of the patient's dentition in the intermediate configuration with the virtual model of the patient's dentition in the final configuration. Alternatively, the dental professional may construct the guide 30 by superimposing the virtual model of the patient's dentition in the beginning configuration with the virtual model of the patient's dentition in the final configuration. Intersection boundaries of the two superimposed virtual models would define the locations of the apertures 36 in the guide 30.

Simulated Veneers

A simulated veneer may be generated automatically for all orthodontic set-ups, including retrospective set-ups, such that a library of models may be created systematically for the purpose of diagnosis and screening for potential veneer cases. The automated models may be measured in terms of, for example, volume, area and thickness, to better characterize the impact of veneer placement to the dentition prior, to initiating treatment. The simulated veneers allow doctors to avoid unnecessary movement of the teeth and removal of excessive amounts of tooth structure.

In one embodiment, orthodontic and prosthodontic procedures may be combined virtually to create simulated veneers. Using an orthodontic procedure, a starting and stopping point for a veneering procedure may be determined. Thus, a virtual simulated veneer may be created using a Final alignment position relative to an Initial tooth position. Thus, the method described uses three points of data: Initial position, simulated or actual Prepared position (tooth material removed), Final alignment position (or any other intermediate position).

The Initial and the Prepared positions are superimposed to determine the difference in volume between the tooth in its Initial position and the tooth in the Prepared position. The difference represents the amount of tooth structure removed (or needed to be removed). Thus:

$$V_r = Vi - V_p$$

where Vj is the initial tooth volume, $V_p$ is the prepared tooth volume, and $V_r$ is the volume removed or preparation volume.

The Initial position and the Final alignment position may also be superimposed relative to a reference to define a sweep path from the Initial position to the Final alignment position for each tooth. The reference may be a static tooth, rugae, gingival and the like. The sweep path defines a swept volume ($V_s$), which represents the union of the prepared tooth volume and restorative structure volume (restoration volume) that is to be created. The swept volume may need to be modified to assure that the swept volume of the tooth does not intersect the swept volume of a neighboring tooth or veneer.

The tool predicts the restoration volume ($V_{res}$) as follows:

$$V_{res} = V_s - Vp$$

where, the $V_p$ is subtracted from the $V_s$ in order to create the total restoration volume, $V_{res}$ The $V_{res}$s, $V_s$, $V_p$, $V_r$ may all be formed as separate geometrical models apart from the tooth. Using features of the tool, the $V_{res}$ (simulated veneer), for example, may be manipulated through shape modification, as well as color modification. The simulated veneer may also be printed as a physical 3-D graphic or formed as a 3-D solid model.

Figure 20:
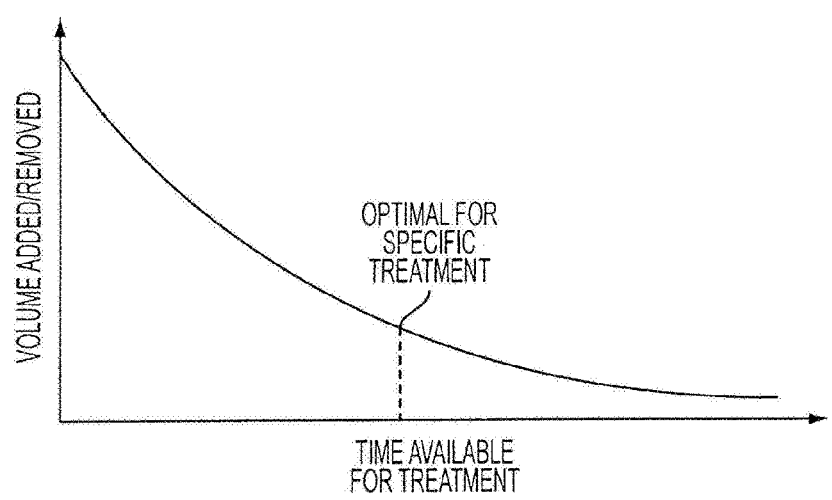
FIG. 20 is a graph representing the start and stop points which yield the least amount of tooth mass removal and/or mass build-up over a given amount of available treatment time.

Advantageously, the veneer-related quantification may be used as the reference for a veneering review, evaluation and analysis. The quantification may include, but is not limited to, volume, thickness, area and the like. The quantified results may be used to automatically or manually select the optimal start point and stop point of a veneering treatment. In addition, the ability to visualize the quantified results provides a reference for a doctor or patient to select the preferable veneering option. For example, as illustrated in the graph of FIG. 20, the doctor and patient can determine the optimal start and stop point, which yields the least amount of tooth mass removal and/or mass build-up over a given amount of available treatment time. Optimality also includes the probability of achieving the Final alignment position for a given type of malocclusion in the available treatment time. It should be understood that available treatment time equates to an amount of tooth movement that may be realized during the available treatment time.

Figure 21:
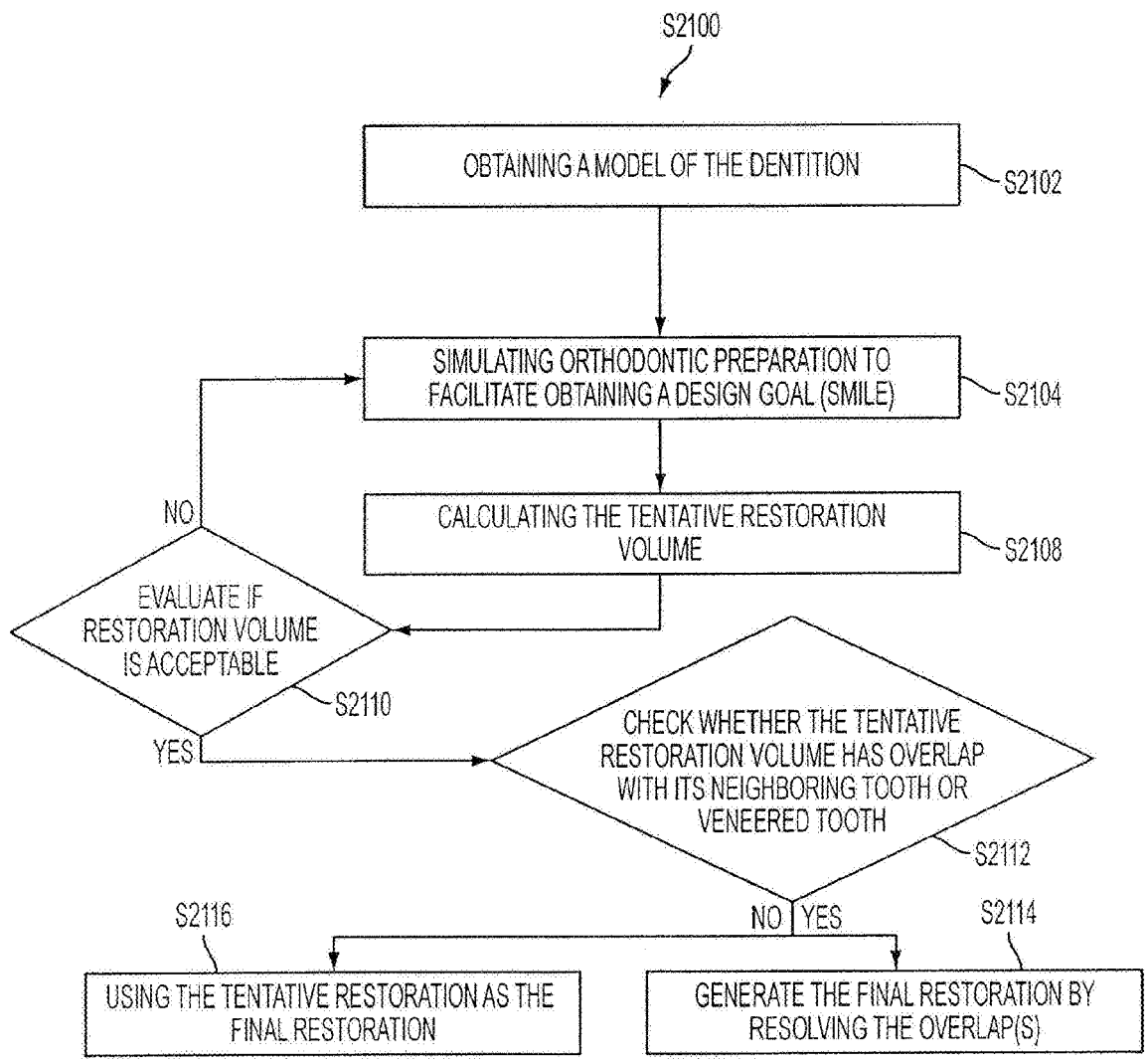
FIG. 21 is a flowchart illustrating a process for simulating the creation of veneer models using orthodontic and prosthodontic techniques in accordance with one embodiment of the present invention.
Figure 22A:
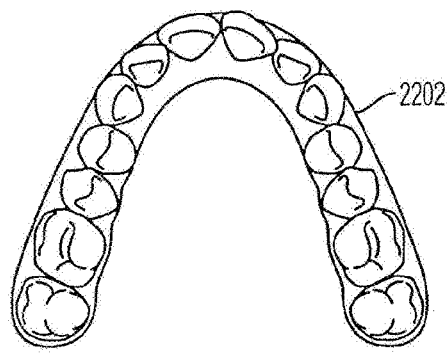
FIGS. 22A and 22B are simplified views of a dental arch in a pre-treatment configuration and in a final configuration in accordance with one embodiment of the present invention, respectively.
Figure 22B:
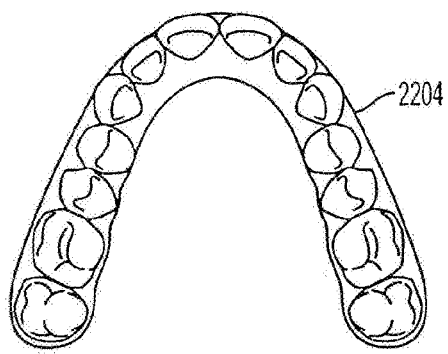

FIG. 21 is a flowchart illustrating a process s2100 for simulating the creation of veneers using orthodontic and prosthodontic techniques. FIGS. 22A and 22B are simplified views of a dental arch in an Initial position and in a Final alignment position, respectively.

Referring to FIGS. 21, 22A and 22B, in step s2102, the dental professional, perhaps in conjunction with a dental laboratory, may create a computer-generated, 3-D, virtual model of the patient's actual dentition in a beginning configuration 2202 (FIG. 22A). The virtual model may be generated prior to any tooth preparation, so that the model represents the patient's dentition in a pretreatment state. Some processes for making such a virtual model are described in, for example, the '207 publication and the '749 application previously incorporated herein by reference.

The dental professional as shown in step s2104, again perhaps in conjunction with the dental laboratory or any other company or service/product provider, may transform the virtual model of the beginning configuration. The dental professional may use virtual orthodontia to create a computer-generated, 3-D, virtual model of the patient's dentition in a Final alignment position or Final configuration 2204 (FIG. 22B), which represents the desired "smile" or design goal that the patient and doctor desire. The virtual orthodontia may include manipulation and movement of teeth in the virtual model. The orthodontic treatment may also include the modeling of several intermediate stages between the beginning configuration and Final alignment position. The beginning configuration or else one of the intermediate stages may be considered an Initial position for starting the veneering treatment as will be explained below.

Figure 23:
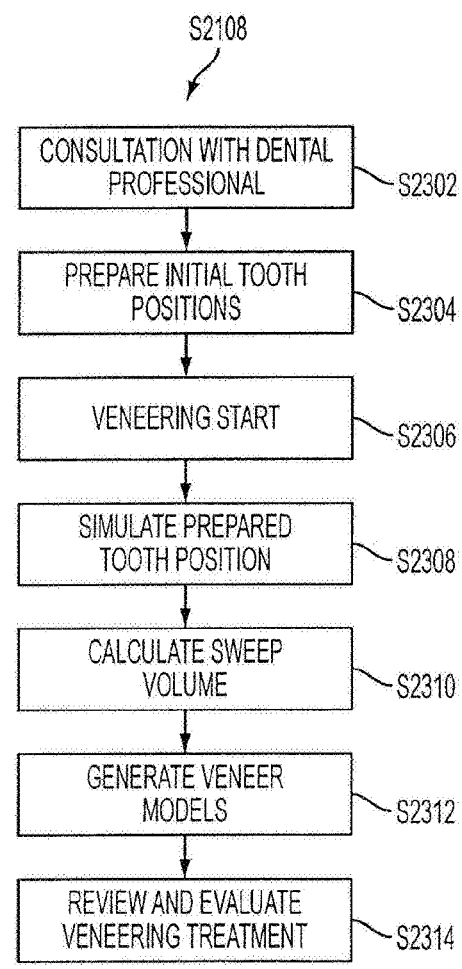
FIG. 23 is a flowchart illustrating steps in an embodiment of the process of FIG. 21.

In step s2108, a tentative restoration volume (simulated veneer) may be calculated for a given time available for treatment. FIG. 23 illustrates an embodiment for calculating the tentative restoration volume of step s2108.

Referring now to FIG. 23, one embodiment of the present methods may begin when a patient first consults a dental professional regarding an orthodontic procedure and/or a prosthodontic procedure (s2302). During the initial consultation, the dental professional and the patient may discuss the patient's treatment goal(s) and any constraints that might limit the time available for treatment. For example, the patient may desire to have his or her smile enhanced, but has only a six-month window of opportunity for treatment. In this situation, the timeframe for treatment is limited, and an appropriate orthodontic/prosthodontic treatment plan must be set to fit within the timeframe.

In the present embodiment, the dental professional may decide that substantially the entire six-month window of treatment time be used to provide a particular amount of tooth movement before starting the veneering treatment. Accordingly, in step s2304, the dental professional, again perhaps in conjunction with the dental laboratory or any other company or service/product provider, simulates orthodontic movement of the teeth between the beginning configuration and an Intermediate position.

In the present embodiment, the Intermediate position represents the starting point or the Initial position for the veneering treatment and is so specified (s2306). Now that the dental professional knows the predicted Initial position of the teeth, the dental professional may determine the Prepared position.

In step s2308, the dental professional, again perhaps in conjunction with the dental laboratory or any other company or service/product provider, may transform the virtual model of the Initial position using virtual prosthodontia to create a computer-generated, 3-D, virtual model of the patient's dentition in a Prepared or cut configuration. The virtual prosthodontics may include the tooth mass removal that the dental professional deems necessary to achieve the design goal (the desired "smile"). The initial Prepared position is referred to hereinafter as the tentative Prepared position.

Figure 24:
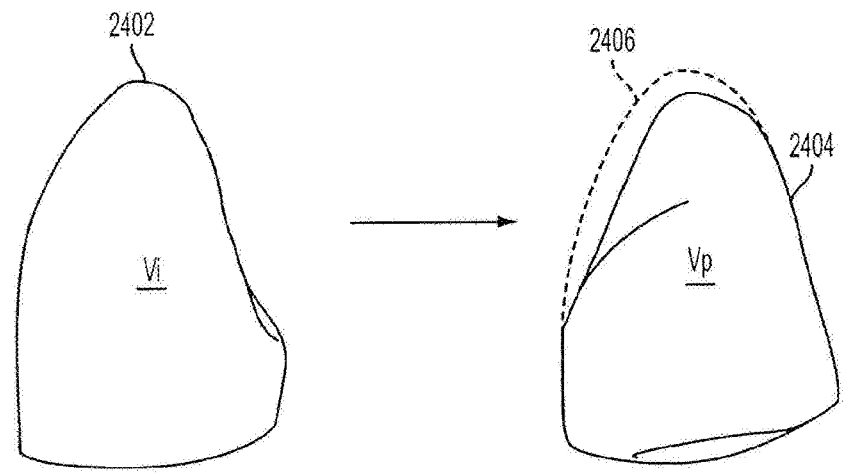
FIG. 24 shows a simplified side view of a tooth in an Initial configuration and a Prepared configuration in accordance with one embodiment of the present invention.

In step s2308, the dental professional may quantify the amount of tooth mass to be removed from the dentition to achieve the desired smile. Referring to FIG. 24, in one embodiment, Intermediate tooth 2402 and Prepared tooth 2404 are superimposed to determine Prepared region 2406, which is the difference in volume between Intermediate tooth 2402 and Prepared tooth 2404. Prepared region 2406 represents the amount of tooth structure to be removed ($V_r$).

Figure 25:
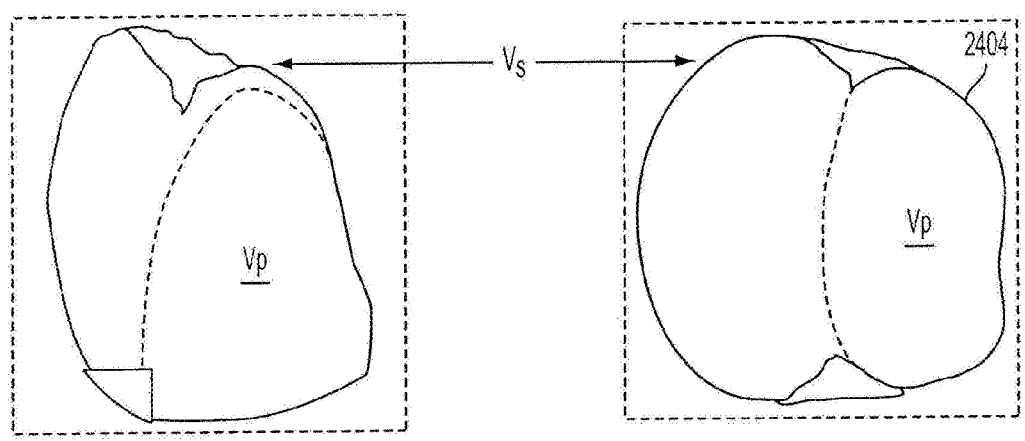
FIG. 25 shows a simplified side view and a top view of the sweep volume of a Prepared tooth configuration in accordance with one embodiment of the present invention.

Referring again to FIG. 23, in step s2310, the dental professional may superimpose the teeth in the Intermediate position with the teeth in the Final alignment position to define a sweep path from the Intermediate position to the Final alignment position for each tooth to be veneered. For example, FIG. 25 is a side view and top view of Prepared tooth 2404 where the swept volume $V_s$ is shown. In this embodiment, swept volume $V_s$ is the space occupied by moving a geometric model of Prepared tooth 2404 along a path from the Intermediate position to the Final alignment position.

Reference is made to the swept volume in the embodiments described, however, one of ordinary skill in the art will understand that many well-known numerical algorithms exist that may be used to generate the envelope model of the Intermediate position and the Final alignment position. For example, such algorithms are referred to as the marching cube, convex hull, maxima, and Boolean union operations. In addition, the swept volume may be estimated analytically.

In step s2312, simulated veneers are generated as separate geometric models apart from the Prepared tooth.

In step s2314, the simulated veneer may be evaluated by reviewing the quantified measurements and visualizing the final geometry of the simulated veneers. For example, Preparation region 2406 is calculated which represents the amount of tooth structure to be removed in preparing the teeth. Also, the total restoration volume is calculated by subtracting the Prepared tooth volume from the sweep volume to create the total restoration volume. The simulated veneers may be visualized to facilitate any shape modification, color modification or any other modification that the dental professional deems appropriate.

Referring again to FIG. 21, once a tentative restoration volume has been calculated (s2108), a decision is made in step s2110 as to whether the restoration volume is acceptable to the dental professional and/or the patient. In some cases, for example, the dental professional or patient may decide that the restoration volume is too large or that the amount of tooth structure required to be removed is too great. In these cases, the process may return to the orthodontic simulation step s2104 where the dental professional attempts to modify the design goal, which may include manipulating the movement of the teeth to lessen the concerns of the dental professional and patient.

In cases where the tentative restoration is acceptable, the process continues to step s2112, where a check is made to determine if the swept volume may need to be modified to assure that the sweep volume of the tooth does not overlap the swept volume of a neighboring tooth or veneer.

In step s2114, if overlap does exist, the overlap needs to be resolved. One approach to remove the overlap is to deform or locally modify the overlap area of the veneer model.

In step s2116, if there is no overlap, the tentative restoration is deemed to be the final restoration and may be subsequently made into an actual restoration.

Figure 26:
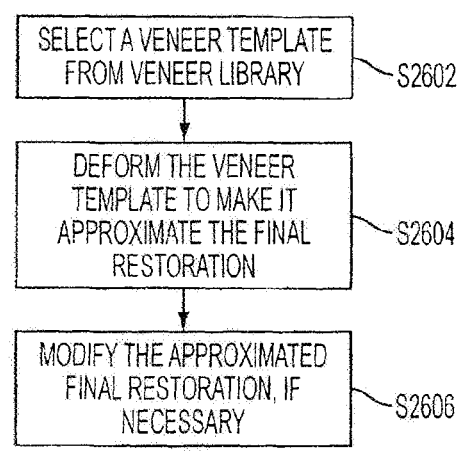
FIG. 26 is a flowchart illustrating a process for preparing an actual restoration in accordance with the present invention.

Referring now to FIG. 26, as shown in step s2602, to create an actual restoration from the final restoration, a veneer template may be selected from a veneer library, which includes all types, shapes and sizes of veneers. The veneer template provides a reference geometry for the modeling of the actual restoration. The reference geometry of the veneer template may be a 3D digital model. Generally, the veneer template may be defined by various physical parameters, such as height, width, thickness and the like.

As shown in step s2604, after a veneer template has been selected, the veneer template may be used to generate the actual veneer shape model (actual restoration) by deforming the veneer template to approximate the final restoration model. When the physical parameters of the veneer template are changed, the geometry of the actual restoration changes. The deformation may be achieved through the adjustment of the physical parameters, 3D morphing and the adjustment of the control points on the template surface.

As shown in step s2606, after the actual veneer shape model is generated, if necessary, the actual veneer shape model may be further locally modified automatically or interactively to satisfy any clinical requirements and user preferences.

Once the actual veneer shape model, with any modifications, has been generated, it may be made into a physical veneer. In one embodiment, the physical veneer may be created by creating the reverse veneer with a template, filling the template with a dental material, such as acrylic, composite, silicone, and the like, in the uncured state and then curing the dental material, creating the physical veneer in the desired shape. In one alternative embodiment, the physical veneer may be built up directly in wax with a 3-D printer. The wax may then be invested and cast into, for example, porcelain or glass, using the lost-wax technique. In another alternative embodiment, the physical veneer may be converted directly into a CAD-CAM object that may be milled from a block of porcelain or glass.

The following points may be considered aspects of the present disclosure:

Point 1. A method for developing a dental treatment plan comprising: (a) creating a virtual model of a dental patient's dentition in a beginning configuration, the dentition including teeth; (b) transforming the virtual model of the dentition using virtual orthodontics from the beginning configuration into an intermediate configuration; (c) transforming the virtual model of the dentition using virtual prosthodontics from the intermediate configuration into a final configuration, the final configuration including the teeth and a dental restoration; (d) transforming the dentition from the beginning configuration into the intermediate configuration; (e) performing at least one of tooth surface removal, tooth cutting and tooth reshaping on the dentition; and (f) affixing the dental restoration to the dentition.

Point 2. The method of point 1, further comprising: g) identifying and evaluating a restorative parameter.

Point 3. The method of point 2, further comprising iterating steps b), c) and g).

Point 4. The method of point 2, wherein the restorative parameter is a volume of tooth material to be removed, an aesthetic feature, or a configuration of interior portions of the dentition Point 5. The method of point 2, further comprising: h) determining whether the restorative parameter meets a desired threshold.

Point 6. The method of point 5, further comprising creating an orthodontic plan based upon the beginning configuration, the intermediate configuration and the final configuration.

Point 7. The method of point 6, further comprising creating an orthodontic appliance based upon the orthodontic plan.

Point 8. The method of point 1, further comprising creating a restorative goal based upon the beginning configuration, the intermediate configuration and the final configuration.

Point 9. The method of point 8, further comprising creating a prosthodontic preparation based upon the restorative plan.

Point 10. The method of point 1, wherein transforming the actual dentition from the beginning configuration into the intermediate configuration comprises the use of at least one dental aligner.

Point 11. The method of point 1, further comprising verifying the efficacy of the at least one of tooth surface removal, tooth cutting and tooth reshaping.

Point 12. The method of point 11, wherein verifying comprises positioning a preparation guide over the dentition and measuring a clearance between a tooth and the preparation guide.

Point 13. The method of point 12, wherein the preparation guide is substantially congruent to the final configuration of the dentition.

Point 14. The method of point 12, wherein the preparation guide includes at least one aperture that enables a portion of the tooth to protrude beyond a wall portion of the preparation guide.

Point 15. The method of point 11, wherein verifying comprises positioning the dental restoration on the dentition and verifying a proper fit.

Point 16. The method of point 15, further comprising repeating step e) when the dental restoration does not fit properly on the dentition.

Point 17. A method for preparing a dental treatment plan comprising: creating a virtual model of a dental patient's dentition, the dentition including teeth; transforming the virtual model of the dentition using virtual prosthodontics to yield a desired outcome relative to at least one restorative parameter; iterating on the transforming step until substantially achieving the desired outcome relative to the at least one restorative parameter; and generating a prosthodontic treatment plan based upon the substantially achieved treatment goal.

Point 18. The method of point 17, wherein the at least one restorative parameter comprises a volume of tooth material to be removed, an aesthetic feature, a configuration of interior portions of the dentition, or a combination thereof.

Point 19. The method of point 17, wherein iterating on the transforming step comprises: transforming the virtual model of the dentition using virtual orthodontics to facilitate substantially achieving the desired outcome relative to the at least one restorative parameter.

Point 20. A preparation guide for use during a prosthodontic procedure, comprising: a virtually generated overlay configured to cover at least a portion of teeth in a patient's upper or lower arch, the overlay including a wall portion forming at least one cavity configured to receive the teeth; wherein the wall portion includes at least one aperture configured to receive a protruding portion of the teeth.

Point 21. The preparation guide of point 20, wherein the virtual overlay is configured to cover all teeth in a patient's upper or lower arch.

Point 22. A method of fabricating a preparation guide for use during a prosthodontic procedure comprising: creating a first virtual model of a patient's dentition in a beginning configuration; manipulating the virtual model using computer software to create a second virtual model of the patient's dentition in a desired final configuration; superimposing the first and second virtual models; identifying, in the superimposed models, intersection boundaries at areas where the dentition of the first model protrudes beyond the dentition of the second model; and fabricating the preparation guide to substantially conform to the second model and having apertures defined by the intersection boundaries.

Point 23. The method of point 22, further comprising the step of reviewing the second virtual model with the patient.

Point 24. The method of point 23, further comprising the step of manipulating the second virtual model to arrive at an alternate desired final configuration.

Point 25. A method for developing a dental treatment plan, the method comprising: (a) creating a virtual model of a dental patient's dentition in a beginning configuration, the dentition including teeth; (b) identifying at least one parameter of the dental treatment program to be controlled so that the parameter falls within a desired range; (c) transforming the virtual model of the dentition using at least one of virtual orthodontics and virtual prosthodontics from the beginning configuration into a final configuration; (d) evaluating the effect of the transforming step on the parameter; and (f) repeating steps b), c) and d) until the transforming step produces a desired effect on the parameter.

Point 26. The method of point 25, wherein identifying at least one parameter of the dental treatment program to be controlled so that the parameter falls within a desired range comprises identifying a plurality of parameters of the dental treatment program to be controlled so that the plurality of parameters fall within desired ranges.

Point 27. A method for generating dental information of a patient comprising: creating a virtual model of a patient's dentition in a first configuration, the dentition including at least one tooth having a reference volume; generating a model volume created as the at least one tooth travels from the first configuration to a second configuration; and subtracting the reference volume from the model volume to yield a build-up volume.

Point 28. The method of point 27, further comprising creating a virtual model of a patient's dentition in a prepared configuration.

Point 29. The method of point 28, further comprising determining a removed volume by subtracting a volume of the dentition in the prepared configuration from the reference volume.

Point 30. The method of point 29, further comprising determining a restoration volume by combining the removed volume and the build-up volume.

Point 31. The method of point 28, further comprising: transforming the virtual model of the patient's dentition from the first configuration into a first intermediate configuration; generating a first intermediate model volume created as the at least one tooth travels from the first intermediate configuration to the second configuration; subtracting the reference volume from the first intermediate model volume to yield a first intermediate build-up volume; and evaluating the effect of the transforming step on the first intermediate build-up volume to determine if the effect is a desired effect.

Point 32. The method of point 31, further comprising: determining a removed volume by subtracting a volume of the dentition in the prepared configuration from the reference volume; and determining a restoration volume by combining the removed volume and the first intermediate build-up volume.

Point 33. The method of point 31, further comprising: transforming the virtual model of the patient's dentition from the first configuration into a second intermediate configuration; generating a second intermediate model volume created as the at least one tooth travels from the second intermediate configuration to the second configuration; subtracting the reference volume from the second intermediate model volume to yield a second intermediate build-up volume; and evaluating the effect of the transforming step on the second intermediate build-up volume to determine if the effect is a desired effect.

Point 34. The method of point 33, further comprising: determining a removed volume by subtracting a volume of the dentition in the prepared configuration from the reference volume; and determining a restoration volume by combining the removed volume and the second intermediate build-up volume.

Point 35. The method of point 27, wherein generating the model volume comprises: determining the volume of the virtual space occupied by the at least one tooth as the at least one tooth travels from the first configuration to the second configuration.

Point 36. The method of point 27, further comprising: verifying whether the build-up volume overlaps a neighboring virtual tooth volume or virtual veneer volume.

Point 37. The method of point 36, further comprising: deforming the build-up volume to resolve the overlap.

Point 38. The method of point 27, wherein creating the virtual model of a patient's dentition comprises generating a reference contour mesh crown representing the surface boundary of the at least one tooth.

Point 39. The method of point 38, wherein generating the model volume comprises: calculating the virtual space occupied by the reference contour mesh crown as the reference contour mesh crown travels from the first configuration to the second configuration.

Point 40. A system for generating dental information of a patient comprising a processor configured to: create a virtual model of a patient's dentition in a first configuration, the dentition including at least one tooth having a reference volume; generate a model volume created as the at least one tooth travels from the first configuration to a second configuration; and subtract the reference volume from the model volume to yield a build-up volume.

Point 41. The system of point 40, wherein the processor is further configured to create a virtual model of a patient's dentition in a prepared configuration.

Point 42. The system of point 41, wherein the processor is further configured to determine a removed volume by subtracting a volume of the dentition in the prepared configuration from the reference volume.

Point 43. The system of point 42, wherein the processor is further configured to determine a restoration volume by adding the removed volume and the build-up volume.

Point 44. The system of point 40, wherein the processor is further configured to: transform the virtual model of the patient's dentition from the first configuration into a first intermediate configuration; generate a first intermediate model volume created as the at least one tooth travels from the first intermediate configuration to the second configuration; subtract the reference volume from the first intermediate model volume to yield a first intermediate build-up volume; and evaluate the effect of the transform step on the first intermediate buildup volume to determine if the effect is a desired effect.

Point 45. The system of point 44, wherein the processor is further configured to: transform the virtual model of the patient's dentition from the first configuration into a second intermediate configuration; generate a second intermediate model volume created as the at least one tooth travels from the second intermediate configuration to the second configuration; subtract the reference volume from the second intermediate model volume to yield a second intermediate build-up volume; and evaluate the effect of the transform step on the second intermediate build-up volume to determine if the effect is a desired effect.

Point 46. The system of point 40, wherein the processor is further configured to: verify whether the build-up volume overlaps a neighboring virtual tooth volume or virtual veneer volume.

Point 47. The system of point 46, wherein the processor is further configured to: deform the build-up volume to resolve the overlap.

Point 48. The system of point 40, further comprising a mechanism for displaying a virtual representation of the first configuration, the build-up volume, the restoration volume, the removed volume, the second configuration, the final configuration, the prepared configuration or the reference volume.

The flowcharts provided herein illustrate example embodiments of the present methods. In some alternative embodiments, the steps shown in one or more figures may occur out of the order presented. For example, in some cases, two steps shown in succession may be executed substantially concurrently, or the steps may sometimes be executed in the reverse order. Those of ordinary skill in the art will also appreciate that the scope of the present methods is defined only by the claims provided below, and therefore some embodiments may not include all of the steps shown in the figures.

The above description presents the best mode contemplated for carrying out the present prosthodontic and orthodontic apparatus and methods, and of the manner and process of making and using them, in such full, clear, concise, and exact terms as to enable any person skilled in the art to which it pertains to make these apparatus and use these methods. These apparatus and methods are, however, susceptible to modifications and alternate constructions from those discussed above that are equivalent. Consequently, these apparatus and methods are not limited to the particular embodiments disclosed. On the contrary, these apparatus and methods cover all modifications and alternate constructions coming within the spirit and scope of the apparatus and methods as generally expressed by the following claims, which particularly point out and distinctly claim the subject matter of the apparatus and methods.

What is claimed is:

1. A method of planning a dental treatment for one or more teeth of a patient, the method comprising:
    receiving a three-dimensional virtual model for the one or more teeth of the patient in a beginning configuration, the received three-dimensional virtual model representing an actual dentition of the patient;
    producing a series of dental treatment options based on the received three-dimensional virtual model, at least one of the series of dental treatment options including (1) an orthodontic treatment for moving one or more teeth of the patient from the beginning configuration to an intermediate configuration and (2) a prosthodontic treatment for transforming the one or more teeth from the intermediate configuration to a final configuration;
    rating each of the series of produced dental treatment options against one or more restorative parameters;
    outputting each of the series of produced dental treatment options along with its rating against the one or more restorative parameters;
    receiving a user selection of one of the series of produced dental treatment options; and
    outputting instructions, according to the selected dental treatment option, for producing at least one of (1) a series of orthodontic aligners, and (2) a preparation guide.

2. The method of claim 1, wherein the one or more restorative parameters include a lingual alignment.

3. The method of claim 1, wherein the one or more restorative parameters include a period time for performing the dental treatment.

4. The method of claim 1, wherein the one or more restorative parameters include an amount of tooth structure removal.

5. The method of claim 1, wherein the one or more restorative parameters include a tooth color.

6. The method of claim 1, wherein the one or more restorative parameters include a veneer thickness.

7. The method of claim 1, wherein at least one of the series of dental treatment options includes at least one orthodontic only treatment option.

8. The method of claim 1, wherein rating each of the series of produced treatment options against one or more restorative parameters comprises assigning qualitative values to each of the one or more restorative parameters.

9. The method of claim 1, wherein at least one of the series of dental treatment options further includes at least one prosthodontic only treatment option.

10. The method of claim 1, wherein the orthodontic treatment is produced by applying virtual orthodontics to the received three-dimensional virtual model, and wherein the prosthodontic treatment is produced by applying virtual prosthodontics comprising one or more modifications to the received three-dimensional virtual model, the one or more modifications comprising at least one of a virtual tooth mass removal, a virtual build up, and a virtual placement of one or more dental restorations.

11. A method of planning a dental treatment for one or more teeth of a patient, the method comprising:
   receiving a virtual model for the one or more teeth of the patient in a beginning configuration, the received three-dimensional virtual model representing an actual dentition of the patient;
   receiving a constraint on a restorative parameter for the dental treatment;
   planning an orthodontic treatment based on the received three-dimensional virtual model and comprising a tooth movement of one or more teeth of the patient from the beginning configuration to an intermediate configuration according to the constraint on the restorative parameter;
   planning a prosthodontic treatment based on the intermediate configuration of the teeth of the patient to transform the teeth of the patient from the intermediate configuration to a final configuration, wherein the prosthodontic treatment is planned so that the dental treatment satisfies the received constraint on the restorative parameter; and
   outputting instructions for producing at least one of (1) a series of orthodontic aligners according to the planned orthodontic treatment, and (2) a preparation guide according to the planned prosthodontic treatment.

12. The method of claim 11, wherein the restorative parameter comprises a time for performing the dental treatment, and wherein the orthodontic treatment is planned according to a constraint on the time for the dental treatment.

13. The method of claim 11, wherein the restorative parameter comprises an amount of tooth structure removal, and wherein the orthodontic treatment is planned according to a constraint on the amount of tooth structure removal.

14. A method of planning a dental treatment for one or more teeth of a patient, the method comprising:
   receiving a three-dimensional virtual model for the one or more teeth of the patient in a beginning configuration, the received three-dimensional virtual model representing an actual dentition of the patient;
   planning a prosthodontic treatment for treating one or more teeth of the patient using the received three-dimensional virtual model, the planned prosthodontic treatment including applying virtual prosthodontics comprising one or more modifications to the received three-dimensional virtual model, the one or more modifications comprising at least one of a virtual tooth mass removal, a virtual build up, and a virtual placement of one or more dental restorations;
   evaluating a restorative parameter for the planned prosthodontic treatment;
   after evaluating the restorative parameter, planning an orthodontic treatment for treating one or more teeth of patient to move one or more teeth of the patient from the beginning configuration to an intermediate configuration prior to the prosthodontic treatment to improve the evaluation of the restorative parameter;
   revising the planned prosthodontic treatment to transform the one or more teeth of the patient teeth from the intermediate configuration to a final configuration; and
   outputting instructions for producing at least one of (1) a series of orthodontic aligners according to the planned orthodontic treatment, and (2) a preparation guide according to the revised planned prosthodontic treatment.

15. The method of claim 14, wherein the restorative parameter comprises a time for performing the dental treatment.

16. The method of claim 14, wherein the restorative parameter comprises an amount of tooth structure removal.

17. The method of claim 16, wherein evaluating the restorative parameter comprises superimposing the intermediate configuration with the final configuration and determining the amount of tooth structure removal based on the superimposed intermediate and final configurations.

18. The method of claim 17, wherein evaluating the restorative parameter further comprises identifying, on the superimposed intermediate and final configurations, one or more intersection boundaries at areas where the intermediate configuration protrudes beyond the final configuration.

19. The method of claim 14, wherein the restorative parameter comprises a veneer thickness.

20. The method of claim 14, wherein evaluating the restorative parameter for the planned prosthodontic treatment comprises determining whether the restorative parameter falls within a desired range.

* * * * *